United States Patent [19]

Ghedini et al.

[11] Patent Number: 4,608,018
[45] Date of Patent: Aug. 26, 1986

[54] APPARATUS FOR CLEANING IN PARTICULAR TEETH

[76] Inventors: Luigi Ghedini, Via Iussi, 43, 40068 S.Lazzaro Di Savena (BO); Rubbini Claudio, Via Galeazza, 9, 40132 Bologna; Grillini Mauro, Via Piave, 7, 40068 S.Lazzaro Di Savena (BO), all of Italy

[21] Appl. No.: 703,729

[22] Filed: Feb. 21, 1985

[30] Foreign Application Priority Data

Apr. 30, 1984 [IT] Italy ................................. 3445 A/84
Oct. 12, 1984 [IT] Italy ................................. 3602 A/84

[51] Int. Cl.$^4$ ............................................... A61C 5/04
[52] U.S. Cl. ................................................... 433/88
[58] Field of Search ................................ 433/125, 88

[56] References Cited

U.S. PATENT DOCUMENTS 2,814,877 12/1957 Tilden ................................. 433/88
4,412,402 11/1983 Gallant ............................... 433/88

Primary Examiner—Robert Peshock
Attorney, Agent, or Firm—Laff, Whitesel, Conte & Saret

[57] ABSTRACT

Disclosed herein is an apparatus for cleaning in particular teeth, that operates in accordance with the mechanical sandblasting principle and is equipped with a barrel provided with a multiple nozzle, and with means of connection identical to those of a dentistry turbodrill. In order to obtain a gas-powder mixture that is permanently constant or, through control means, is rendered variable, the handgrip of the barrel is fashioned hollow and divided into a receiving chamber, a swirl precombustion chamber and a swirl chamber communicating via elements having a calibrated passage hole. The powder and a small quantity of gas are inserted into the receiving chamber, while the major quantity of gas in inserted into the swirl precombustion chamber through a powder percentage regulator.

9 Claims, 9 Drawing Figures

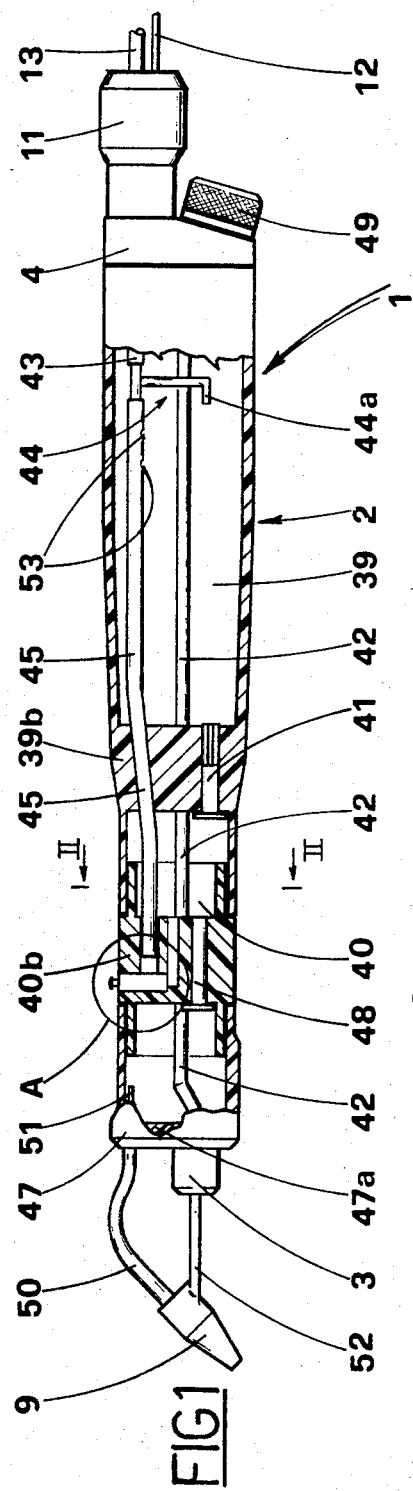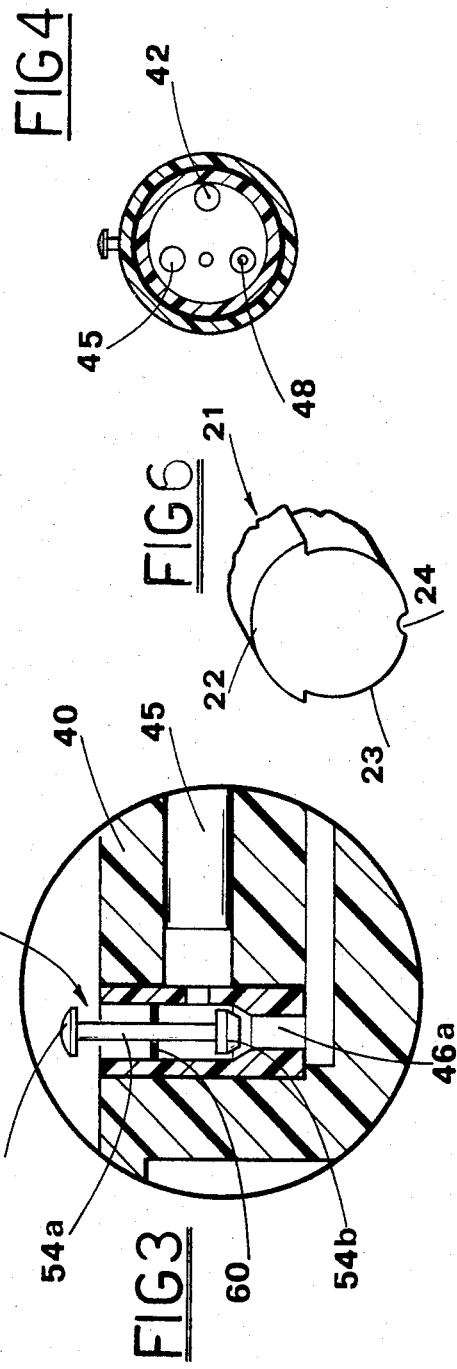

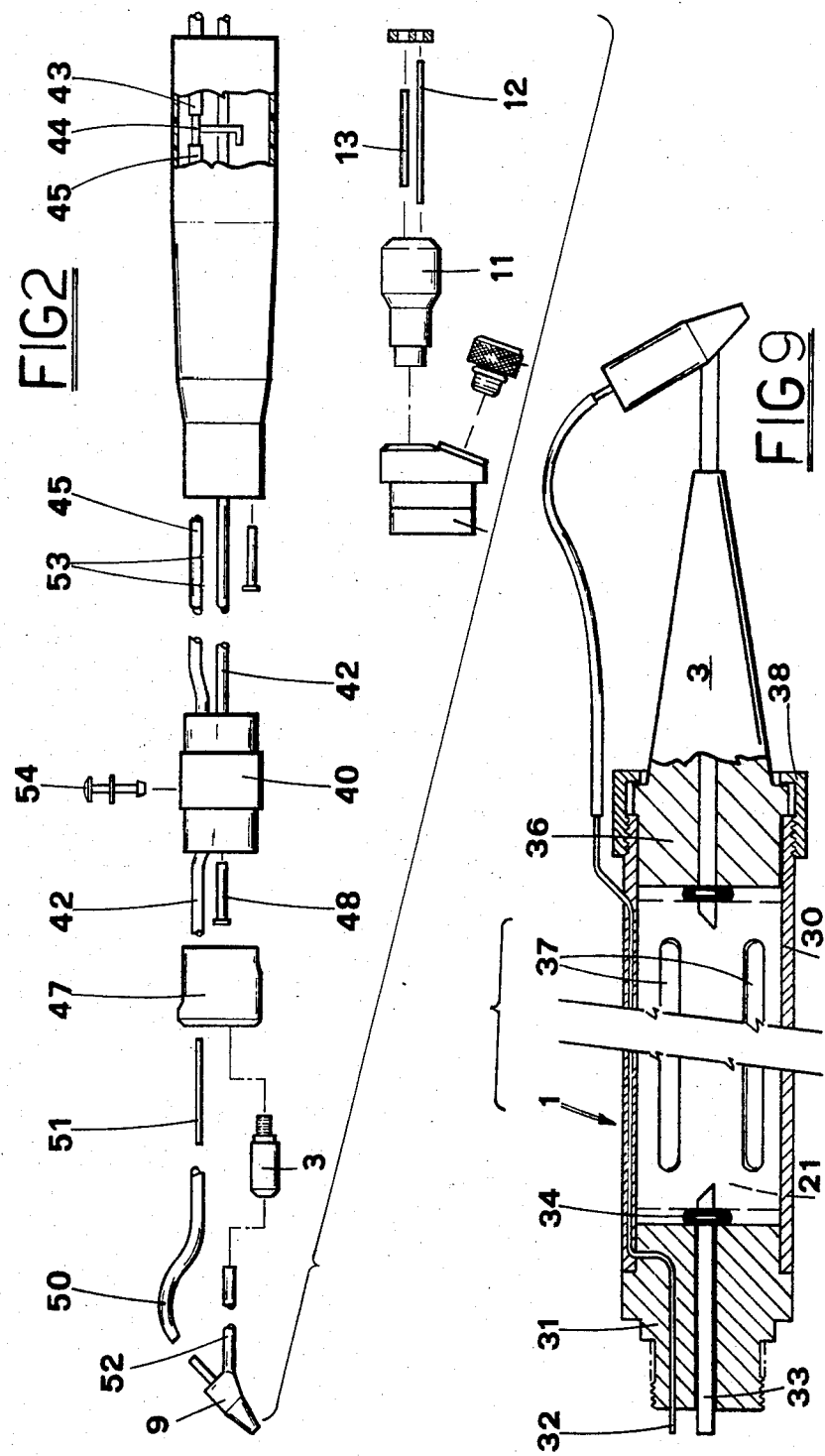

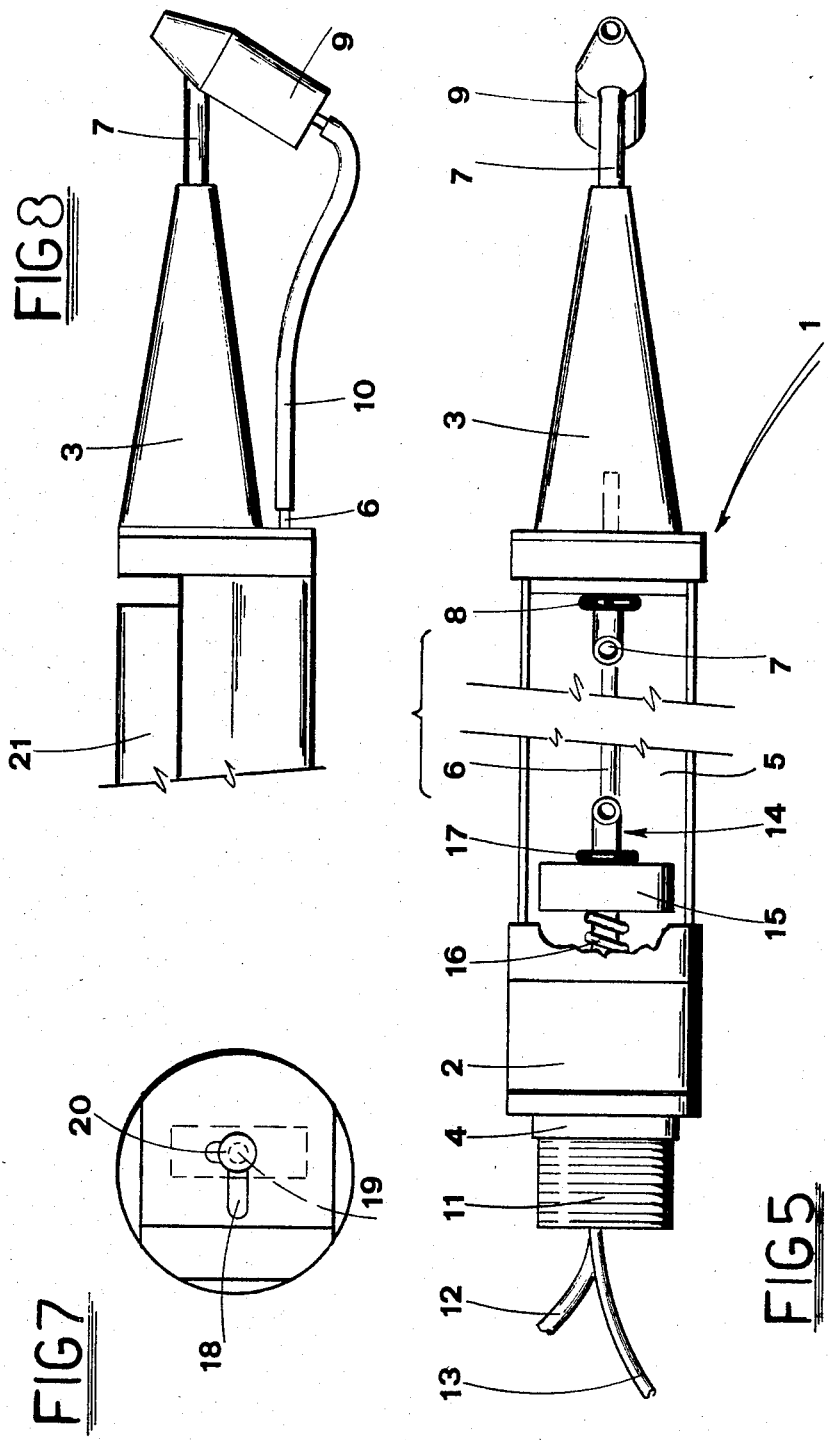

APPARATUS FOR CLEANING IN PARTICULAR TEETH

BACKGROUND OF THE INVENTION

The invention relates to an apparatus for cleaning in particular teeth that operates in accordance with the mechanical sandblasting principle.

DESCRIPTION OF THE PRIOR ART

Various items of equipment are known in the teeth cleaning field that operate in various ways, for example ultrasonically or in conformity with the mechanical sandblasting methods.

Those for which the latter system has been adopted, this having been seen to be more efficient and reliable, are provided with a barrel having a multiple nozzle from which issue under pressure, a jet of water and a jet of a gas mixed with abrasive powder in suspension. The jet of water that issues from the said multiple nozzle enshrouds the jet of gas was the suspension powder and performs, in this way, a cleansing and refreshing action, as can be see in U.S. Pat. No. 3,882,638.

Initially the gas utilized was air, and the powder was sand but later on, since at the end of the treatment the mouth of the patient was filled with sand, thoughts turned (see for example U.S. Pat. No. 4,174,571) to the use, as the abrasive powder, of a soluble product (such as sodium bicarbonate) that dissolves perfectly and rapidly in water.

Despite this solution having proved excellent for patients because of the product dissolving very quickly in water, it is not devoid of problems of sufficient an entity to cause the design and construction of the items of equipment to be complex and costly. As the abrasive powder carrying gas, use is, in fact, generally made, and this for obvious reasons of cheapness and hygiene, of air which always contains a certain quantity of humidity. To prevent the connection and infeed tube from constantly getting blocked, it has, therefore, been necessary to provide the equipment with delicate devices for limiting the humidity in the air since it is extremely difficult to be able to avail oneself of outgoing air from the compressor that is completely dry.

SUMMARY OF THE INVENTION

The technical task of the invention is, therefore, to make available an apparatus for cleaning, and in particular for cleaning teeth, that is free from the problems experienced with the present items of equipment.

Within the framework of this technical task, the object of the invention is to make available an apparatus for cleaning teeth that enables considerable savings to be made production-wise, yet is perfectly functional without giving rise to problems as time goes by.

A further object of the invention consists in making available an apparatus in which it is possible, through control means, to vary the composition of the gas-powder mixture to suit the needs of the user.

The technical task and the said objects are achieved with the apparatus according to the invention for cleaning in particular teeth, that operates in accordance with the mechanical sandblasting principle and is equipped with a barrel provided with a multiple nozzle through which are directed, against the surface to be cleaned of the teeth, one or more jets of gas with abrasive powder in suspension and one or more jets of water, the said apparatus differing from others on account of the fact that the said barrel comprises a handgrip provided with a cavity for receiving a charge of abrasive powder, and means of connection for gas and water under pressure; into the said cavity running supply means, connected to the said nozzle at one end and to the said means of connection, for receiving the air, at the other.

It is obvious that with apparatus of this nature blockage problems do not occur or, at the most, are limited purely to the nozzle which can be cleaned with the utmost simplicity in a short space of time.

The advantages achieved with the invention consist essentially in the fact that the charging of the apparatus is highly practical and economical since the powder, not necessarily sodium bicarbonate, can be contained in ordinary bags and be inserted, via the hole provided, into the powder mixing-receiving chamber.

Another advantage is achieved on account of the fact that the mixture is always of the same composition that can be varied, in the sense of increasing the percentage of powder, only when necessary.

A further advantage lies in the fact of it being possible to utilize, inside the said cavity in the barrel, an interchangeable cartridge so dimensioned as to contain sufficient powder for one single treatment, in such a way that there is no risk, when the apparatus is not in use, of the nozzle getting blocked.

BRIEF DESCRIPTION OF THE DRAWINGS

The invention is described in greater detail in the text that follows, with the aid of the accompanying drawings wherein one embodiment is depicted by way of an example, and in which:

FIG. 1 shows, in a lateral view partially in sectional form, the barrel mounted of the apparatus according to the invention;

FIG. 2 shows, again in a lateral view, the said barrel of FIG. 1 stripped down into the essential elements thereof;

FIG. 3 shows, in an enlarged scale, the detail A in FIG. 1;

FIG. 4 shows, in an enlarged scale, a section along the line II—II of FIG. 1;

FIGS. 5 and 9 show, using a powder containment cartridge, two different alternatives for the apparatus in question;

FIG. 6 shows, in a perspective view, the cartridge;

FIGS. 7 and 8 show, in detail, parts depicted in FIG. 5.

DESCRIPTION OF THE PREFERRED EMBODIMENT

In FIGS. 1 to 4 is shown a barrel 1 composed of a handgrip 2, a rear cylinder 4 and a multiple nozzle 9 at the front. The rear cylinder 4 is provided with means of connection (hidden in the figures) that engage with a nut 11. At these means of connection, that are perfectly identical to those of a turbodrill, terminate outside the barrel 1, the pipes 12 and 13, the former for supplying water and the latter for supplying air, both under pressure. The multiple nozzle 9 is supported, through a rigid tube 52, by a nozzle holder 3, in turn sustained at the front by the handgrip. At the nozzle holder 3 terminates a tube 42 that crosses the handgrip 2 and is connected to the water supply pipe 12. From the front part of the handgrip 2 projects, furthermore, a tube 51 that communicates, externally to the handgrip and through a flexible tube 50, with the multiple nozzle 9.

In conformity with the invention, the handgrip 2 is hollow and constituted by three elements in such a way as to be divided into three successive areas 39a, 40a and 47a, hereinafter referred to as the receiving chamber 39, the swirl precombustion chamber 40 and the swirl chamber 47, respectively.

The receiving chamber 39 is closed on one side by the rear cylinder 4, and on the other by a wall 39b of separation from the successive swirl precombustion chamber 40.

Below the nut 11, the rear cylinder 4 is provided with a hole sealed with a plug 49: powder is inserted into the receiving chamber 39 through the said hole.

Passing through the receiving chamber 39, besides the tube 42, is a pair of successive tubes 43 and 45 that communicate through a T shaped element 44. The element to which reference has just been made receives air from the pipe 13 through the tube 43 and passes the major quantity onto the tube 45, discharging the remainder, that is to say the minor quantity, into the receiving chamber 39 through a nozzle 44a. For the reason that will be explained later on, the tube 45 has, in the region of the receiving chamber 39, a number of holes 53.

The wall 39b that divides the receiving chamber 39 from the swirl precombustion chamber 40 is crossed by an element 41 having a calibrated passage hole, for example a jet.

Provided in the swirl precombustion chamber 40 is a powder percentage regulator 46 at which terminates the tube 45 coming from the receiving chamber 39. The regulator 46 is illustrated as having a pusbutton 54 with a control rod 54a that is provided (see the embodiment example illustrated in FIG. 3) at one extremity with an element 54b for sealing a discharge hole 46a of the regulator 46, and is supported by a diaphragm 60 which, subjected to the action of the air fed in by the tube 45, keeps the control rod 54a, and consequently the sealing element 54b, far away from the discharge hole 46a in such a way that the regulator 46 be fully open.

In a similar way, a wall 40a that divides the swirl precombustion chamber 40 from the swirl chamber 47 is crossed by an element 48 having a calibrated passage hole, for example a jet. As can be seen in FIG. 1, the tubes 42, 43 and 45 do not follow rectilinear paths, this being for assembly reasons.

The element shown at 47a and constituting the swirl chamber 47 is provided at the front with the nozzle holder 3 and the tube 51. This tube runs internally into the swirl chamber 47 and thus passes the air-powder mixture onto the multiple nozzle 9.

The operation of the apparatus in question takes place as follows.

The sealing plug 49 is removed and powder is inserted into the receiving chamber 39 via the hole rendered open through the removal of the plug 49. The said plug is screwed on anew and gas, generally air, and water under pressure are supplied, the former via the pipe 13 and the latter via the pipe 12. The water arrives directly at the multiple nozzle 9 from the pipe 12, through the tube 42, the nozzle holder 3 and the rigid tube 52. A small part of the air coming from the pipe 13 is, instead, deviated inside the receiving chamber 39, through the tube 43, the T shaped element 44 and the nozzle 44a, while the bulk passes into the swirl precombustion chamber, through the T shaped element 44, the tube 45 and the regulator 46. The small quantity of compressed air inserted into the receiving chamber 39 causes a modicum of powder to issue there from through the jet 41. Once in the swirl precombustion chamber 40, this powder is subjected to turbulence and to a greater pressure, and then thrust across the jet 48. From the swirl chamber 47, where still subjected to turbulence, the air-powder mixture arrives at the multiple nozzle 9, and issues there from in the form of a jet. With the presence of the said succession of chambers at various pressures, the concentration of the air-powder mixture discharged from the multiple nozzle 9 is continuously the same irrespective of the degree to which the receiving chamber 39 is filled.

Should a greater cleaning effect, and thus a greater percentage of powder in the air-powder mixture, be required, all that has to be done is to depress the pushbutton 54 of the regulator 46, thereby causing the extent to which the regulator 46 is open and the flow of air into the swirl precombustion chamber 40, to be reduced. In consequence, the pressure of the air in the receiving chamber 39 increases and, in this case, the air issues through the holes 53 in the tube 45. This produces incremented turbulence in the receiving chamber 39 and, therefore, an increase in the quantity of powder that passes across the jet 41 and, ultimately, across the multiple jet 9. When the pushbutton 54 of the regulator 46 is released, normal conditions of pressure and operation are re-established.

With reference to FIG. 5, a description now follows of a barrel in which a powder containment cartridge is utilized. In this case, the barrel is subdivided into a handgrip 2, a front nozzle holder 3 and a rear cylinder 4. The handgrip 2 is of cylindrical tubular shape and is provided with a longitudinal slot 5, rectangular when seen in a plan view, and the reason for this will become apparent hereinafter. The nozzle holder 3 is shaped, at the rear, in the form of a cylinder, and at the front in the form of a cone offset with respect to the cylindrical section.

The cylindrical section of the nozzle holder 3 engages with one extremity of the handgrip 2 and is crossed by a tube 6 parallel to the axis thereof. The conical section of the nozzle holder 3 is crossed axially by a tube 7 that also runs across the cylindrical section of the said nozzle holder 3.

Mounted on the tube 7, inside the handgrip 2, is a gasket 8, for example an O ring, and the extremity of the said tube is cut obliquely in order to exercise, as will be seen below, a better perforating action. Fitted onto the other extremity, outside the handgrip 2 of the tube 7 is a multiple nozzle 9 at which also terminates a tube 10 for the connection thereof to the tube 6.

The rear cylinder 4 engages with the other extremity of the handgrip 2 and is provided, externally to this, with known means of connection restrained by a nut 11. The said means of connection are perfectly identical to those of a known dentistry turbodrill, and thus the barrel described herein can be fitted thereto in place of the turbodrill barrel.

The nut 11 serves to restrain a joint for the two pipes 12 and 13, hidden by the said nut, to the means of connection of the rear cylinder 4.

Running across the said rear cylinder 4, parallel to the axis of this, is a tubular element 14 that terminates at the pipe 13, and a non-illustrated tube that terminates at the pipe 12 and commences at the tube 6. The said tubular element 14 is able to slide along the rear cylinder 4 and carries threaded thereon, on the opposite sides of an annular distended part thereof, shown at 15, a spring 16 and a gasket 17, respectively, the latter for example an O ring. The spring 16 presses against the rear cylinder 4 and thrusts the tubular element 14 towards the inside of the handgrip 2. The terminal part of the tubular element 14 turned towards the nozzle holder 3 is of wedge shape for the reason that will become apparent in the ensuing text. The handgrip 2 is provided with a slot 18 that is longitudinal and has the terminal part turned towards the nozzle holder 3 bent in the form of a hook. A pin 19 connected to the distended part 15 of the tubular element 14 fits into the slot 18 and has, on the outside of the handgrip 2, a head 20.

A cartridge 21 filled with abrasive powder is inserted into the handgrip 2 through the slot 5. In FIG. 9, the cartridge 21 that contains, for example, sodium bicarbonate, is shown with dashes, and in FIG. 6 the particular conformation of the cartridge can be seen. The said cartridge is, in fact, provided with a section 22 whose bending radius corresponds to the outside radius of the handgrip 2, and a section 23 whose bending radius corresponds to the inside radius of the handgrip 2. Furthermore, the section 23 of the cartridge 21 has a recess 24 that receives the tube 6. Shaped in this way, the cartridge 21 can be inserted into the cavity 5 in the handgrip 2 and closed therein without the aid of a cover and, additionally, when the insertion of the cartridge 21 into the slot 5 in the handgrip 2 has taken place, the said handgrip can be seen to be perfectly cylindrical.

For the insertion of the cartridge 21 it is necessary to cause the element 14 to be displaced towards the rear, and this is done by compressing the spring 16 through the head 20 of the pin 19. Once the cartrige 21 is in place, the tubular element 14 is made to slide forward until the cartridge is perforated by this one side, and by the tube 7 on the other side. At this juncture, the apparatus forming the subject of the invention is ready to be used once. With the apparatus set in motion by the turbodrill, the nozzle 9 is supplied with water through the pipe 12, the tube 6 and the tube 10, and with air through the pipe 13, the tubular element 14, the cartridge 21 and the tube 7. Passing across the cartridge 21, the air carries there with, towards the nozzle 9, the abrasive powder contained in the said cartridge 21. In the case of the abrasive powder being sodium bicarbonate, any blockage will be limited solely to the tube 7 and to the multiple nozzle 9, items these that can be cleaned quickly without any difficulty.

In practice, modifications and/or improvements to the apparatus in question can be effected without in any way deviating from the framework of protection afforded to the invention as claimed hereinafter. For example, the barrel may be envisaged more simply with a continuous external surface, and the insertion of the cartridge being either through the upper or the lower extremity, like an ordinary conventional refill.

The said solution is illustrated in FIG. 9, wherein the barrel 1 is constituted by a central body 30, internally hollow and provided, at the rear, with a cylinder 31 coupled to the said body, provided internally with a pair of tubes 32 and 33 that can be connected to the pipes 12 and 13, respectively, coming from the water and air supply of the turbodrill.

The tube 33 runs into the inside of the cavity in the body and has mounted thereon a gasket 34, for example an O ring, while the tube 32 extends longitudinally through the whole body and terminates, laterally and externally, almost in the region of the front extremity of the said body.

At this point is coupled the cylindrical terminal section 36 of the nozzle holder 3 that is rendered integral with the assembly by means of a threaded nut 38.

The said solution enables the interchangeability of the cartridge 21 to be effected in a rational, reliable and rapid way through the removal of just the nozzle holder 3, while the filling state of the said cartridge can be controlled through a plurality of slots 37.

Again in the more simplified case, the cartridge itself can serve as the barrel body; for example, be made in one piece out of plastic material by means of a simple molding operation. In this case two separate chambers are made, both extending longitudinally, one for containing the powder (that is to say acting as a proper tank, and the other (a simple tube similar to the tube 6) for the passage of water.

This cartridge-barrel will have at the extremities thereof, elements of connections, preferably of screw type, that are coupled to the pipes 12 and 13, respectively, and to the nozzle holder 3. In practice, the device becomes of the type that is used and then thrown away.

What is claimed is:

1. An apparatus for cleaning teeth with water, air and a dental cleaning powder comprising a handgrip, a multiple nozzle, a water supply means connected at one end to said nozzle and at said other end adapted to be connected to a source of pressurized water, said handgrip defining a powder chamber and at least one mixing chamber, means to supply pressurized air to said powder chamber, means to supply pressurized air and powder to said mixing chamber, and means to connect said mixing chamber to said multiple nozzle.

2. The apparatus of claim 1 comprising at least two swirl mixing chambers being defined by said handgrip, a first swirl chamber being located between a second swirl chamber and said powder chamber, means connecting said first swirl chamber with said second swirl chamber to supply the contents of said second swirl chamber, and said multiple nozzle being connected to said multiple nozzle to supply air and a powder mixture thereto.

3. The apparatus of claim 2 comprising an air supply duct adapted to be connected to a source of pressurized air, said air duct being connected to both said powder chamber and said first swirl chamber to deliver pressurized air to said powder and first swirl chambers, a regulator connected to said handgrip and said duct to regulate the air delivered to said first swirl chamber.

4. Apparatus according to claim 2, wherein the said powder chamber has therein a plug for sealing a hole through which said powder is inserted.

5. Apparatus according to claim 2, wherein said powder chamber is a receiving cavity provided to receive a powder cartridge said receiving cavity and said powder cartridge being shaped to provide for insertion and removal of said powder cartridge from said powder chamber, said air supply means being so shaped as to perforate the opposite sides of the cartridge with one said air supply means being movable in order to insert the cartridge in said receiving cavity in said handgrip.

6. Apparatus according to claim 5, wherein the said supply means are constituted by internally hollow tubes on which are mounted gaskets that seal flush up against the opposite end surfaces of the said cartridge.

7. Appartus according to claim 5, wherein the said cavity extends laterally and longitudinally with respect to said handgrip, and the cartridge is so shaped as to act as a cover sealing said cavity.

8. Apparatus according to claim 6, wherein the said movable element of the supply means is provided with a control lever that can be operated from the outside in order to bring about a longitudinal traversing movement on the part of the said movable element, elastic means being provided to maintain this in a configuration of projection into the inside of the cavity in the said barrel.

9. An apparatus for cleaning teeth with water, air and a dental cleaning powder comprising a handgrip, a multiple nozzle, a water supply means connected at one end to said nozzle and at said other end adapted to be connected to a source of pressurized water, said handgrip defining a powder cartridge chamber, said powder cartridge chamber being sized to receive a powder cartridge containing dental cleaning powder, means to supply pressurized air to said powder cartridge and means to supply pressurized air and powder to said multiple nozzle.

* * * * *